(12) United States Patent
Zhang et al.

(10) Patent No.: US 12,728,026 B2
(45) Date of Patent: Sep. 8, 2026

(54) KNOB-TYPE THUMB PROTECTOR

(71) Applicant: Guangzhou New Design Biotechnology Co. Ltd., Guangzhou (CN)

(72) Inventors: Shaowei Zhang, Guangzhou (CN); Sile Zou, Guangzhou (CN)

(73) Assignee: Guangzhou New Design Biotechnology Co. Ltd., Guangzhou (CN)

( * ) Notice: Subject to any disclaimer, the term of this patent is extended or adjusted under 35 U.S.C. 154(b) by 56 days.

(21) Appl. No.: 18/761,518

(22) Filed: Jul. 2, 2024

(65) Prior Publication Data

US 2025/0367013 A1 Dec. 4, 2025

(30) Foreign Application Priority Data

May 31, 2024 (CN) ......................... 202410692843.6

(51) Int. Cl.
*A61F 5/01* (2006.01)

(52) U.S. Cl.
CPC ..... *A61F 5/0118* (2013.01); *A61F 2005/0197* (2013.01)

(58) Field of Classification Search
CPC .......... A61F 5/0118; A61F 5/013; A61F 5/10; A61F 5/05866; A61F 5/05875; A41D 13/081–088; A41D 19/015; A41D 19/01505; A41D 19/01517; A41D 19/01582; A41D 19/01588
USPC ............................... 602/20–22; 128/878–880
See application file for complete search history.

(56) References Cited

U.S. PATENT DOCUMENTS

2013/0317788 A1* 11/2013 Summit .................. G06F 30/00 703/1
2014/0123440 A1* 5/2014 Capra ....................... A61F 5/01 29/3
2015/0191326 A1* 7/2015 Hall ..................... A43C 11/165 242/396.4
2016/0296359 A1* 10/2016 Stefansson ................ A61F 5/10
(Continued)

FOREIGN PATENT DOCUMENTS

CN 217660331 U 10/2022
CN 218165448 U * 12/2022 ............... A61F 5/01

OTHER PUBLICATIONS

Translation of CN-218165448-U (Year: 2022).*

*Primary Examiner* — Rachael E Bredefeld
*Assistant Examiner* — Seth R. Brown

(57) ABSTRACT

Provided are a knob-type thumb protector, including: a protector main body, a sleeve hole is formed on the protector main body for a thumb to pass through; a first connecting piece, wherein one end of which is connected to one side of the protector main body, and another end is provided with a connecting groove; a second connecting piece, wherein one end of which is connected to another side of the protector main body, and another end for passing through the connecting groove is connected to the first connecting piece to cooperate with the first connecting piece to form a ring sleeve that wraps around a palm; a knob adjusting piece, the knob assembly is installed on the protector main body, and one end of the adjusting rope is connected to one end of the second connecting piece that passes through the connecting groove.

7 Claims, 11 Drawing Sheets

(56) References Cited

U.S. PATENT DOCUMENTS

2022/0218049 A1* 7/2022 Roth ..................... A61F 15/004
2025/0205073 A1* 6/2025 Moy ....................... A61F 13/04

* cited by examiner

KNOB-TYPE THUMB PROTECTOR

CROSS REFERENCE TO RELATED APPLICATION

This application claims priority benefit of Chinese patent Application No. 202410692843.6, filed on May 31, 2024, and the entire contents of which are incorporated herein by reference.

TECHNICAL FIELD

The present disclosure herein relates to the technical field of medical auxiliary devices, and in particular to a knob-type thumb protector.

BACKGROUND

Tenosynovitis is a common inflammation caused by muscle strain in joints, which is caused by improper use of joints or excessive external force on the muscles. Tenosynovitis occurs not only in the wrist joint, but also in the thumb joint. Especially with the rise of mobile games, people irregularly and forcefully press the screen with their thumbs while playing. They often experience thumb pain after playing mobile games for a long time. In severe cases, they may even suffer from thumb tenosynovitis. To alleviate weakness, pain, or soreness in the thumb, there is a type of thumb protector available on the market that can prevent or slow down the occurrence of thumb tenosynovitis or facilitate the recovery from thumb tenosynovitis. However, the ease and convenience of wearing, adjusting the tightness, and comfort of existing thumb protectors still need to be further improved.

SUMMARY

In view of the above, the present disclosure provides a knob-type thumb protector to improve the convenience of wearing and adjusting and the comfort of use.

The technical solutions adopted in the present disclosure are:

a knob-type thumb protector, including:

a protector main body, wherein a sleeve hole is formed on the protector main body for a thumb to pass through, so that the protector main body is sleeved at a base of the thumb to form a structure supporting the thumb;

a first connecting piece, wherein one end of the first connecting piece is connected to one side of the protector main body, and a connecting groove is arranged on another end of the first connecting piece;

a second connecting piece, wherein one end of the second connecting piece is connected to another side of the protector main body, another end of the second connecting piece for passing through the connecting groove is connected to the first connecting piece, and the second connecting piece cooperates with the first connecting piece to form a ring sleeve that wraps around a palm; and a knob adjusting piece, wherein the knob adjusting piece includes a knob assembly and an adjusting rope that is adjustably and telescopically connected to the knob assembly; and the knob assembly is installed on the protector main body, and one end of the adjusting rope is connected to one end of the second connecting piece that passes through the connecting groove, enabling a tightness of the first connecting piece and the second connecting piece to be adjusted by rotating the knob assembly.

Furthermore, one end of the second connecting piece passing through the connecting groove is provided with a hook, so that the adjusting rope is hung on the hook.

Furthermore, the protector main body includes a finger cover portion and a palm supporting portion connected to the finger cover portion in a belt-like shape, the sleeve hole is formed on the finger cover portion, the knob assembly is installed on the finger cover portion, and the palm supporting portion is used to abut against a palm surface.

Furthermore, one end of the first connecting piece is connected to the finger cover portion and is located on an opposite side of the palm supporting portion, and one end of the second connecting piece is connected to the palm supporting portion.

Furthermore, a thumb loop is formed on the sleeve hole, which wraps around an outer periphery of the base of the thumb, providing a certain degree of telescopic elasticity.

Furthermore, the finger cover portion, the palm supporting portion, the first connecting piece and the second connecting piece are all made of a flexible material and are integrally formed.

Furthermore, a hard supporting piece is arranged on outer surfaces of the finger cover portion and the palm supporting portion.

Furthermore, the hard supporting piece is made of a shaped metal material.

Furthermore, the second connecting piece is provided with a plurality of hook mounting holes arranged along its extension direction, so that the hook can be selectively installed.

Furthermore, an end of the first connecting piece is upturned, and a through hole is arranged on an upturned end surface to form the connecting groove, so that the second connecting piece is attached parallel to a surface of the first connecting piece after passing through the connecting groove, and the hook is blocked by a groove wall of the connecting groove.

Furthermore, an arched beam is integrally formed on an end surface of the second connecting piece, the connecting groove is correspondingly formed in a beam hole of the arched beam, and the arched beam can be selectively configured as a disconnected structure.

Furthermore, the hard supporting piece includes a supporting shell wrapped around a back side of the thumb and a supporting strip connected to the supporting shell, the supporting shell is arranged on an outer peripheral surface of the finger cover portion, and the supporting strip is arranged on the outer surface of the palm supporting portion.

Furthermore, the knob assembly includes a base, a wire reel, a sleeve base, a ratchet, a screw cap and a spring, and a holding groove is provided on an inner side of a peripheral wall of the base;

the wire reel is rotationally installed on the base, and a spring mounting hole is arranged on a bottom surface of the wire reel; a rotating tooth distributed annularly around an axis center line and arranged at equal intervals is formed on a top end of the wire reel; an end wall is formed on an upper end of the sleeve base, and a through center hole is arranged on a center of the end wall; a tenon is formed on an outer periphery of a lower end of the sleeve base, and a flange is extended laterally on the outer periphery of the upper end of the sleeve base; the sleeve base is sleeved on an outer periphery of the wire reel, and the tenon extends into the holding groove; the ratchet is fixedly buckled on a top of the sleeve base, and a plurality of ratchet teeth are formed on an outer periphery of the ratchet;

the screw cap is rotationally installed on an outer periphery of the sleeve base, and an inner ring surface of the screw cap is provided with a toothed ring for being sleeved on the outer periphery of the ratchet to cooperate with the ratchet teeth; a matching tooth is formed on an inner surface of the screw cap for cooperating with the rotating tooth of the wire reel; and the spring is installed in the spring mounting hole of the wire reel, which provides an elastic force to lift the wire reel upward, so that in a normal state, the top end of the wire reel is abutted against a top end of the sleeve base, and the matching tooth of the screw cap is cooperated with the rotating tooth of the wire reel;

Furthermore, the knob assembly includes a button, and a sleeve portion is protruded from a central portion of the top end of the wire reel; a button groove is recessed on a central portion of a top surface of the screw cap, a through hole is formed on a bottom of the button groove, the sleeve portion passes through the center hole and the through hole and enters the button groove, and the button is installed in the button groove and is fixedly sleeved on the sleeve portion.

Beneficial effects of the present disclosure:

compared to the prior art, the present disclosure provides a knob-type thumb protector, by setting the protector main body, the first connecting piece, the second connecting piece, and the knob adjusting piece to cooperate with each other; firstly, the protector main body is sleeved on the base of the thumb, and the first connecting piece and the second connecting piece are located in the back side and the inner side of the palm, respectively; then the second connecting piece passes through the connecting groove on the one end of the first connecting piece, and the adjusting rope is adjusted by rotating the knob assembly, thereby driving the second connecting piece to adjust the position along the connecting groove, further enabling the adjustment of the tightness or looseness of the first connecting piece and the second connecting piece when worn on the palm. This makes wearing and adjusting more convenient and more comfortable to use. The knob-type thumb protector provided by the present disclosure has a novel and simple structure, is easy to process and manufacture, and can provide comfortable protection and moderate support for the thumb.

BRIEF DESCRIPTION OF THE DRAWINGS

The accompanying drawings are intended to provide a further understanding of the present disclosure, and they constitute a part of the specification. Together with the following detailed descriptions of embodiments, they are used to explain the present disclosure, but should not be construed as limiting the scope of the present disclosure. In the accompanying drawings.

DETAILED DESCRIPTION OF THE EMBODIMENTS

The embodiments of the present disclosure will be described in detail below with reference to the accompanying drawings. It should be understood that the embodiments described here are only used to illustrate and explain the present disclosure, and are not intended to limit the present disclosure.

Figure 1:
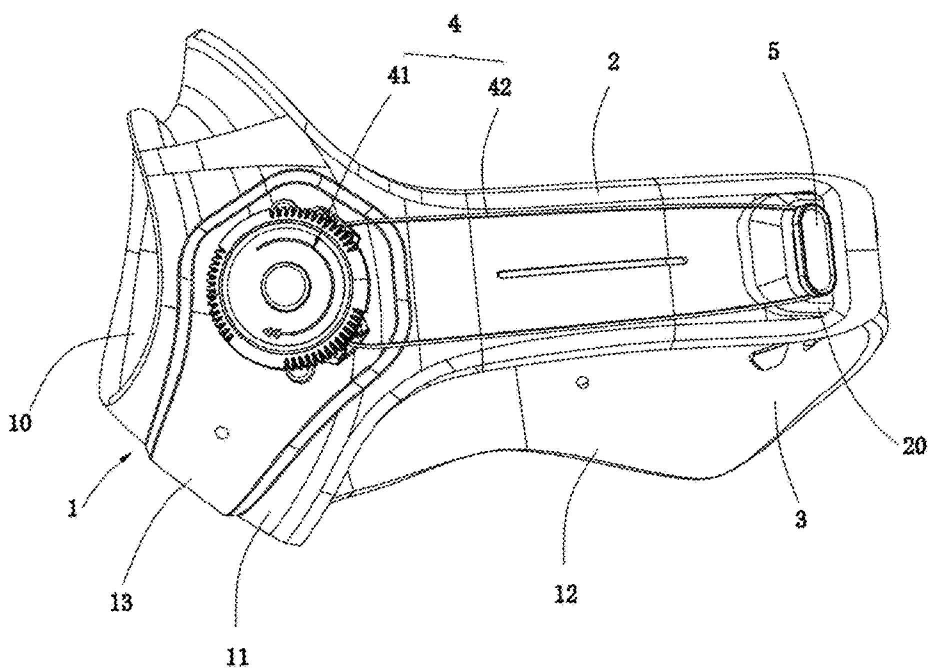
FIG. 1 is a three-dimensional view from the first perspective of a knob-type thumb protector of the present disclosure.
Figure 2:
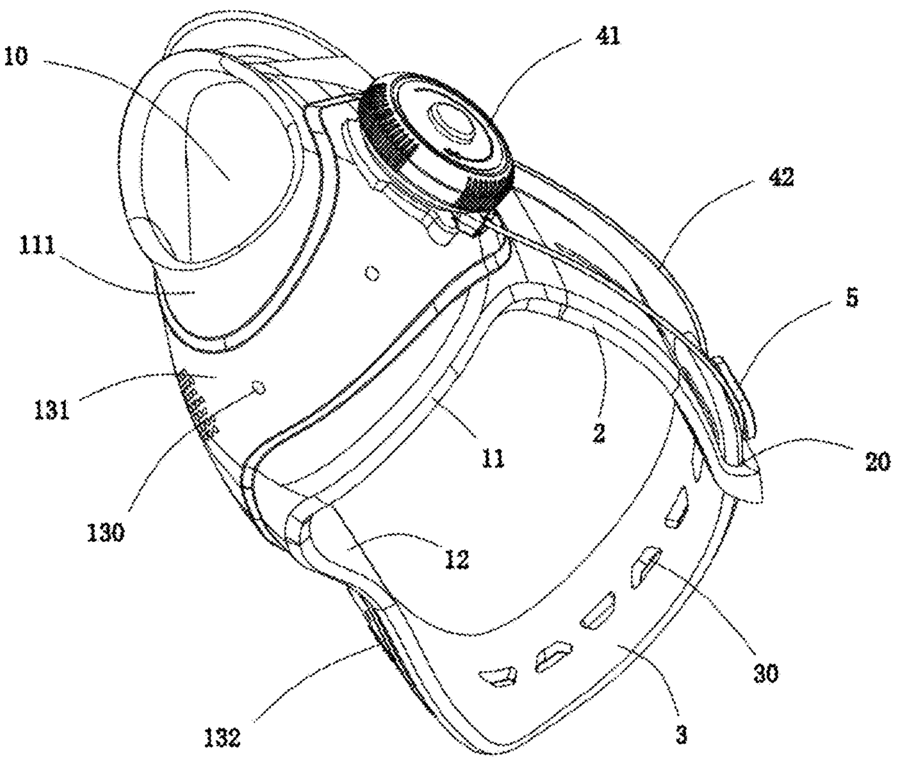
FIG. 2 is a three-dimensional view from the second perspective of a knob-type thumb protector of the present disclosure.
Figure 3:
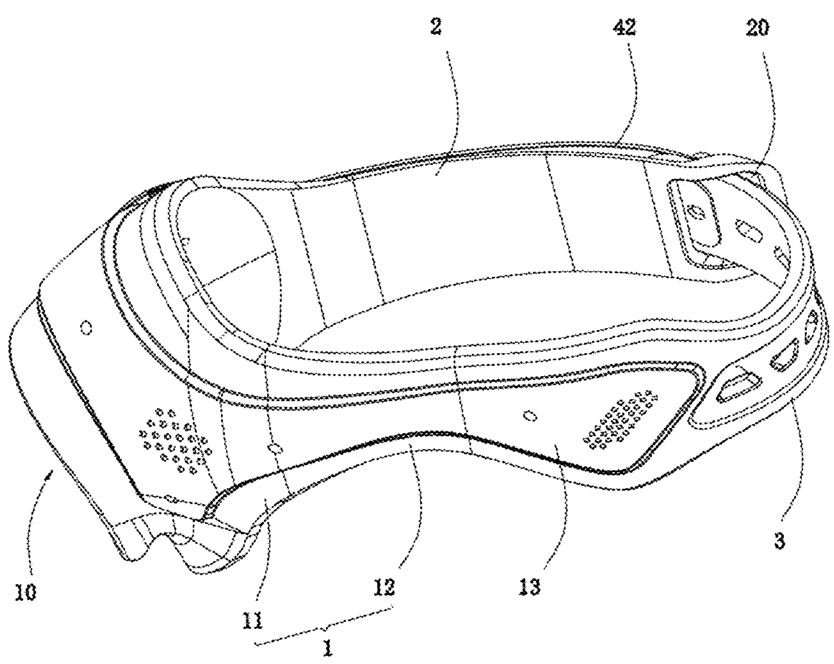
FIG. 3 is a three-dimensional view from the third perspective of a knob-type thumb protector of the present disclosure.

As shown in FIGS. 1 to 3, the present disclosure provides a knob-type thumb protector, which includes a protector main body 1, a first connecting piece 2, a second connecting piece 3 and a knob adjusting piece 4. A sleeve hole 10 is formed on the protector main body 1 for a thumb to pass through, so that the protector main body 1 is sleeved at a base of the thumb to form a structure supporting the thumb. One end of the first connecting piece 2 is connected to one side of the protector main body 1, and a connecting groove 20 is arranged on another end of the first connecting piece 2. One end of the second connecting piece 3 is connected to another side of the protector main body 1, and another end of the second connecting piece 3 for passing through the connecting groove 20 is connected to the first connecting piece 2, forming a sleeve that wraps around a palm. The knob adjusting piece 4 includes a knob assembly 41 and an adjusting rope 42 that is adjustably and telescopically connected to the knob assembly 41. The knob assembly 41 is installed on the protector main body 1, and one end of the adjusting rope 42 is connected to one end of the second connecting piece 3 that passes through the connecting groove 20 to adjust the tightness of the thumb protector worn on the palm by rotating the knob assembly 41.

The present disclosure provides a knob-type thumb protector, by setting the protector main body 1, the first connecting piece 2, the second connecting piece 3, and the knob adjusting piece 4 to cooperate with each other; firstly, the protector main body 1 is sleeved on the base of the thumb via a sleeve hole 10, and the first connecting piece 2 and the second connecting piece 3 are located in the back side of the palm, respectively; then the second connecting piece 3 passes through the connecting groove 20 on the one end of the first connecting piece 2, and the adjusting rope 42 of the knob adjusting piece 4 is connected to one end of the second connecting piece 3 that passes through the connecting groove 20, and the adjusting rope 42 is adjusted by rotating the knob assembly 41, thereby driving the second connecting piece 3 to move and adjust the position along the connecting groove 20, further enabling the adjustment of the tightness or looseness of the first connecting piece 2 and the second connecting piece 3 when worn on the palm. This makes wearing and adjusting more convenient and more comfortable to use. The knob-type thumb protector provided by the present disclosure has a novel and simple structure, is easy to process and manufacture, and can provide comfortable protection and moderate support for the thumb.

In this embodiment, the protector main body 1 includes a finger cover portion 11 and a palm supporting portion 12 for fitting on the palm side. The sleeve hole 10 is formed on the finger cover portion 11, and the palm supporting portion 12 is connected to the finger cover portion 11. Furthermore, a thumb loop 111 is formed on the sleeve hole 10, which wraps around an outer periphery of the base of the thumb, providing a certain degree of telescopic elasticity. One end of the first connecting piece 2 is connected to the finger cover portion 11 and is located on an opposite side of the palm supporting portion 12, and one end of the second connecting piece 3 is connected to the palm supporting portion 12. The knob assembly 41 is installed on the finger cover portion 11. In this way, the palm supporting portion 12 provides effective support to the thumb sleeved in the finger cover portion 11 through the palm, ensuring good comfort of support.

Figure 4:
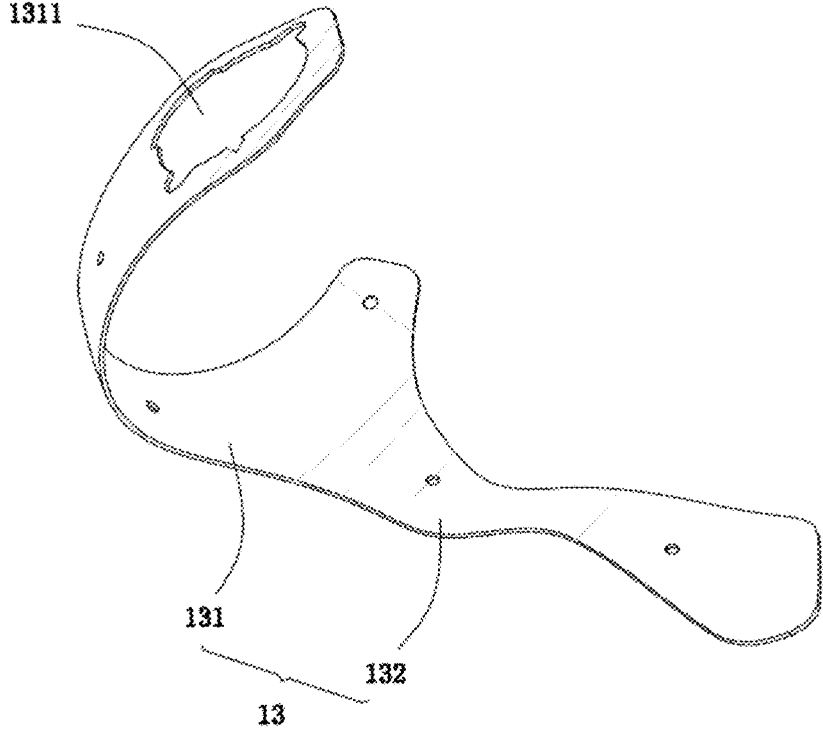
FIG. 4 is a three-dimensional view of a hard supporting piece of a knob-type thumb protector of the present disclosure.

In this embodiment, the finger cover portion 11, the palm supporting portion 12, the first connecting piece 2 and the second connecting piece 3 are all made of flexible materials such as silicone and are integrally formed. A hard supporting piece 13 is arranged on outer surfaces of the finger cover portion 11 and the palm supporting portion 12 for shaping the knob-type thumb protector structure. The hard supporting piece 13 can be made of metal materials such as aluminum, or can also be made of non-metallic materials, all of which have certain plasticity. Specifically, the hard supporting piece 13 includes a supporting shell 131 wrapped around a back side of the thumb and a supporting strip 132 connected to the supporting shell 131, the supporting shell 131 is arranged on an outer peripheral surface of the finger cover portion 11, and the supporting strip 132 is arranged on the outer surface of the palm supporting portion 12. A knob avoidance hole 1311 is formed on the supporting shell 131 for installing the knob adjusting piece 4. Referring to FIG. 4, the supporting shell 131 and the supporting strip 132 of the hard supporting piece 13 can be integrally formed of plastic metal. Furthermore, the supporting shell 131 and the supporting strip 132 are both provided with ventilation holes 130 to improve wearing comfort.

In order to facilitate the connection between the adjusting rope 42 and the second connecting piece 3, one end of the second connecting piece 3 passing through the connecting groove 20 is provided with a hook 5, and a wire groove for holding the adjusting rope 42 is formed between the hook 5 and the second connecting piece 3. In this way, it is convenient to disassemble the adjusting rope 42 hung on the hook 5 and to achieve a stable connection between the adjusting rope 42 and the second connecting piece 3.

Both the first connecting piece 2 and the second connecting piece 3 are in the form of a belt structure, so as to be easily wrapped around both sides of the palm.

It can be understood that the hook 5 is detachably installed on the second connecting piece 3. In order to meet the need for a larger wearing size, furthermore, the second connecting piece 3 is provided with a plurality of hook mounting holes 30 arranged along its extension direction, enabling the hook 5 to be selectively installed on the corresponding hook mounting holes 30, thus adjusting the second connecting piece 3 to have a larger wearing span.

Please refer to FIG. 3 again. It can be understood that in order to facilitate the end of the second connecting piece 3 and the hook 5 to penetrate into the connecting groove 20, the end of the first connecting piece 2 is upturned, and a through hole is arranged on the upturned end surface to form the connecting groove 20, so that the second connecting piece 3 can be attached roughly parallel to the surface of the first connecting piece 2 after passing through the connecting groove 20, and the hook 5 is blocked by the groove wall of the connecting groove 20 to prevent it from exiting the connecting groove 20.

Figure 7:
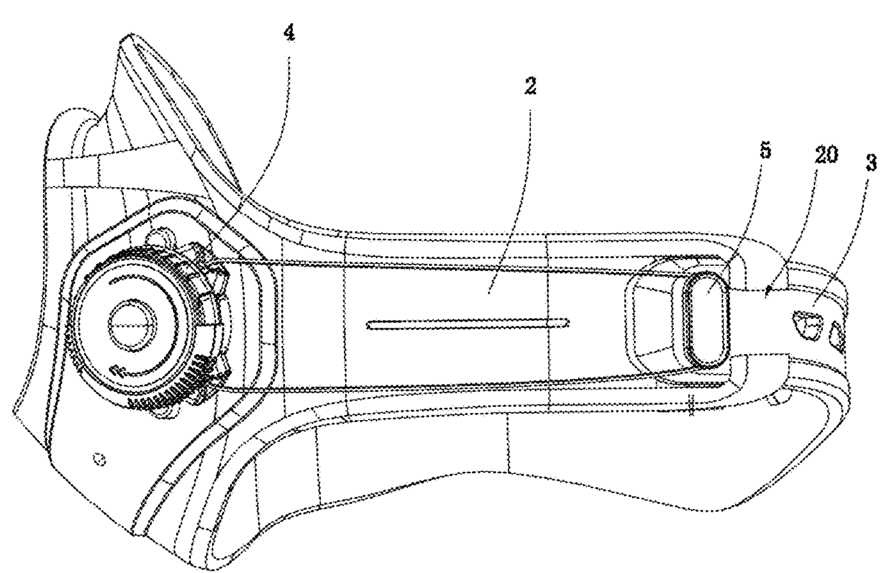
FIG. 7 is a three-dimensional view of another embodiment of a second connecting piece of a knob-type thumb protector of the present disclosure.
Figure 8:
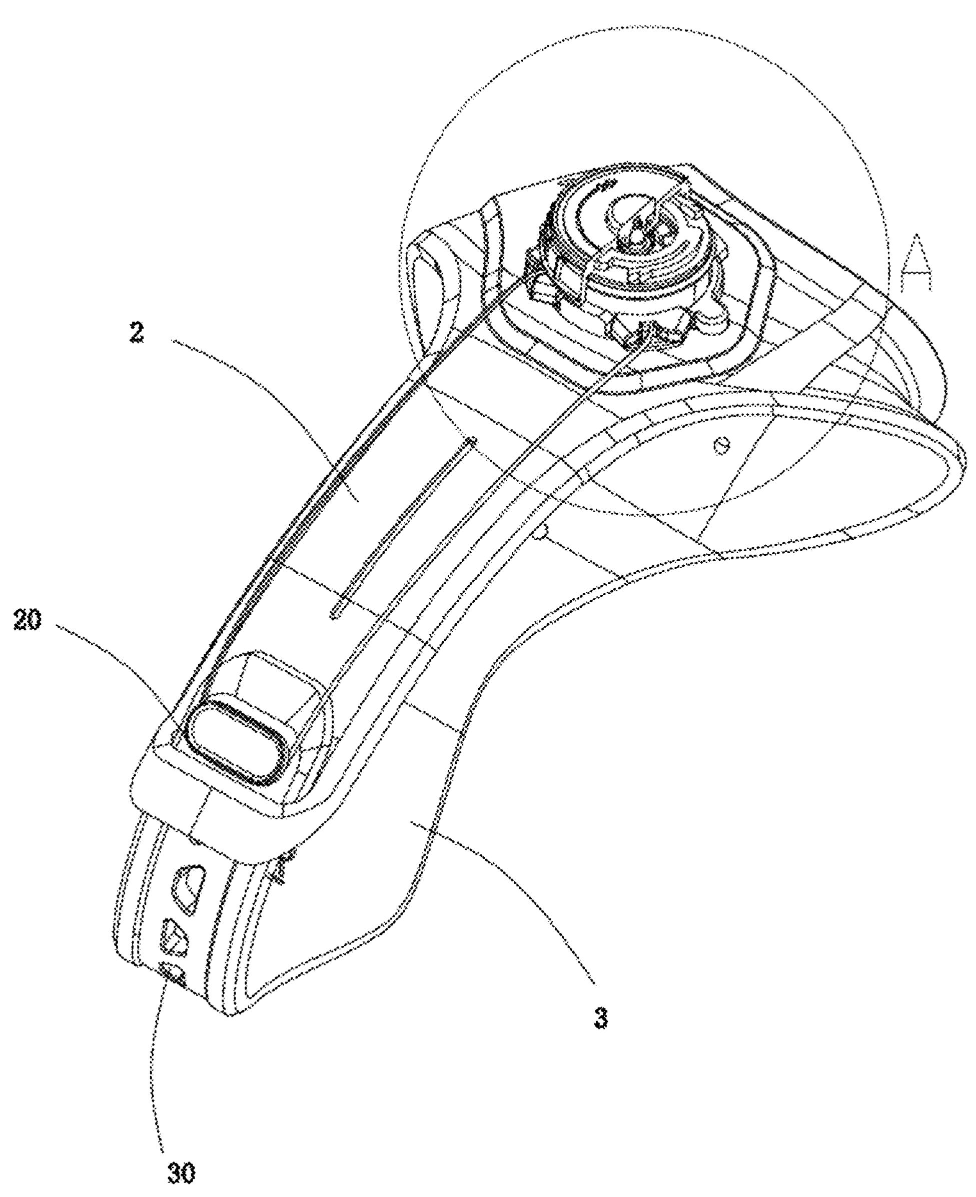
FIG. 8 is a partial sectional view of a knob-type thumb protector of the present disclosure.
Figure 9:
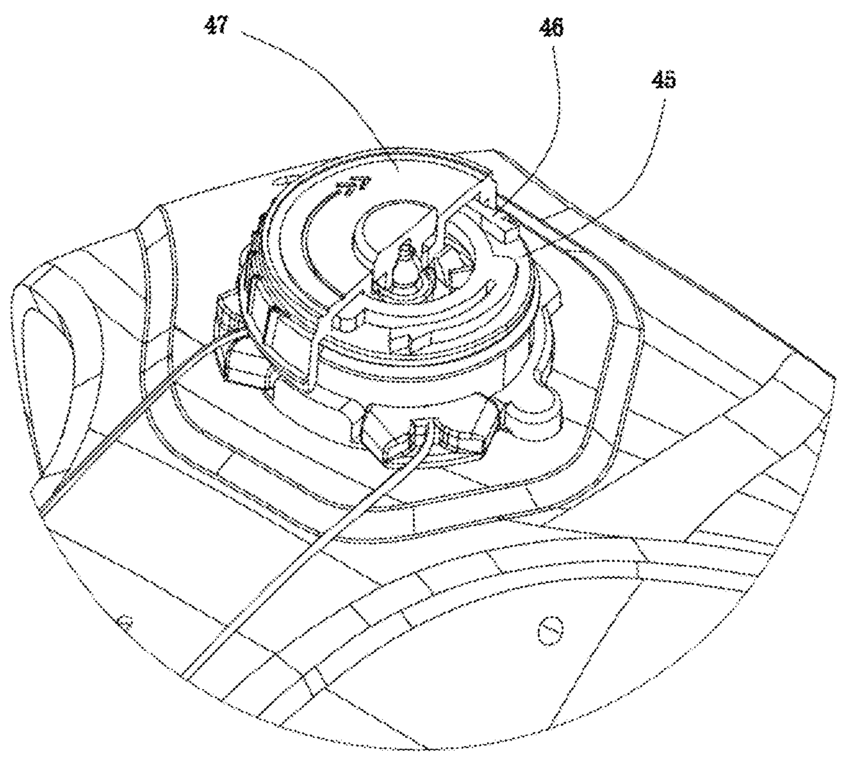
FIG. 9 is an enlarged view of the position A shown in FIG. 8.
Figure 10:
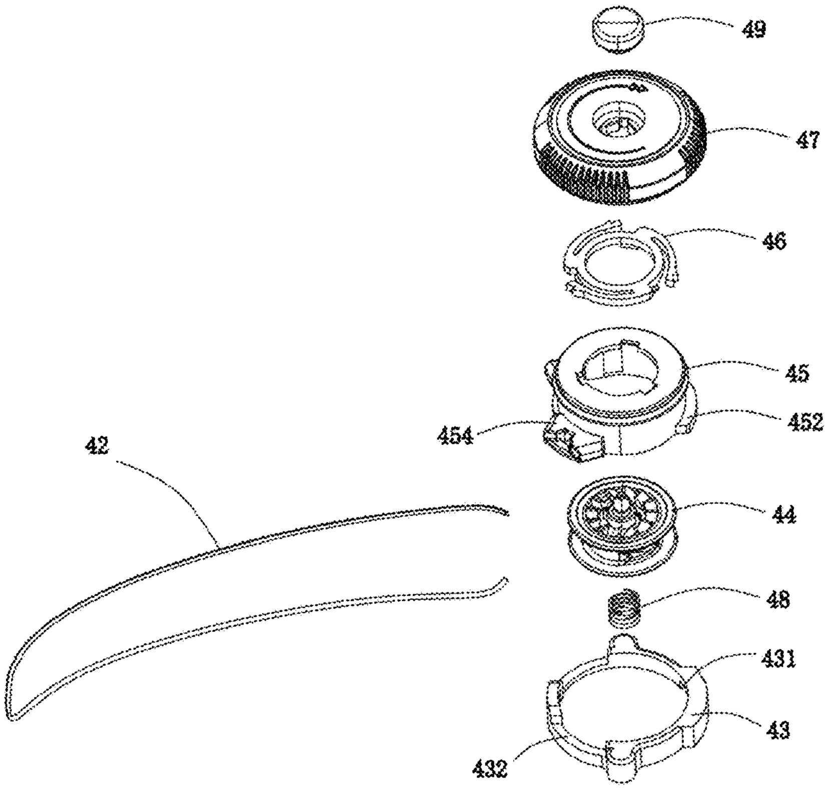
FIG. 10 is an exploded view of a knob adjusting piece of a knob-type thumb protector in a preferred embodiment of the present disclosure.
Figure 11:
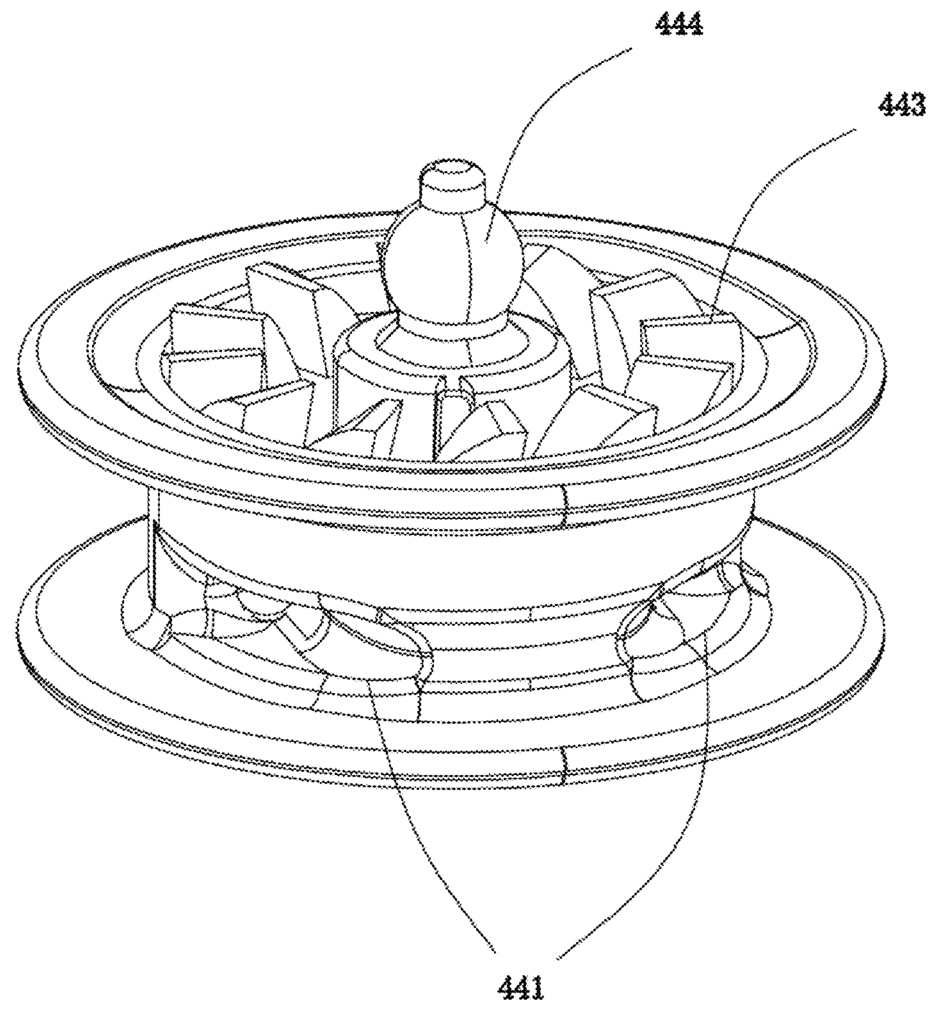
FIG. 11 is a three-dimensional view of a wire reel of a knob assembly in the present disclosure.
Figure 12:
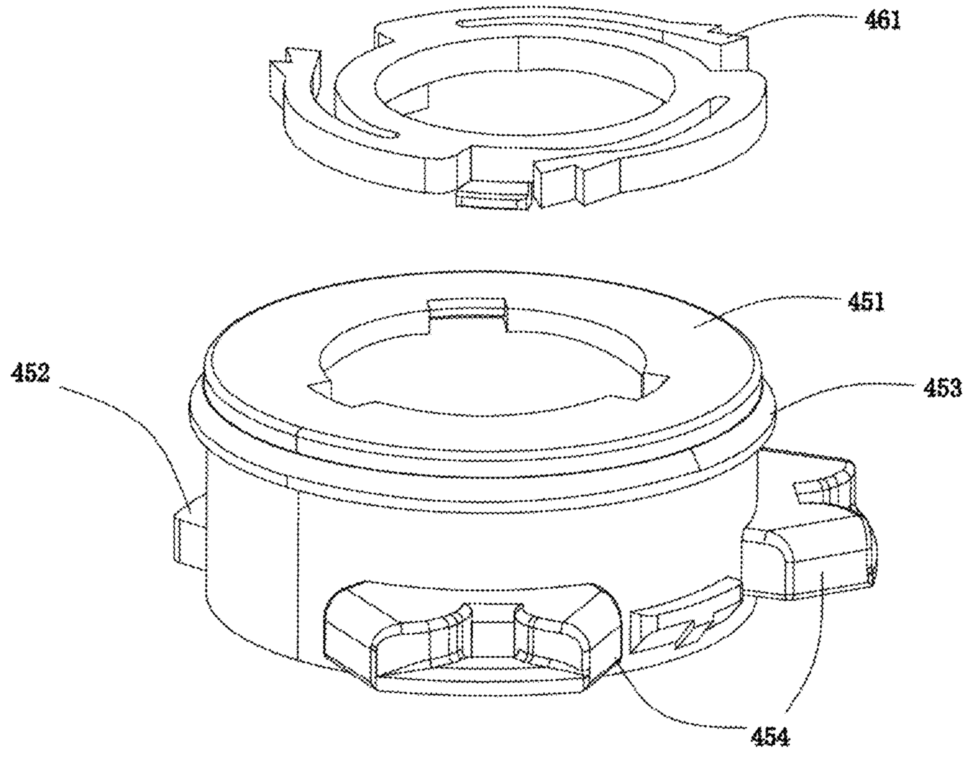
FIG. 12 is a three-dimensional view of a sleeve base cooperating with a ratchet of a knob assembly in the present disclosure.
Figure 13:
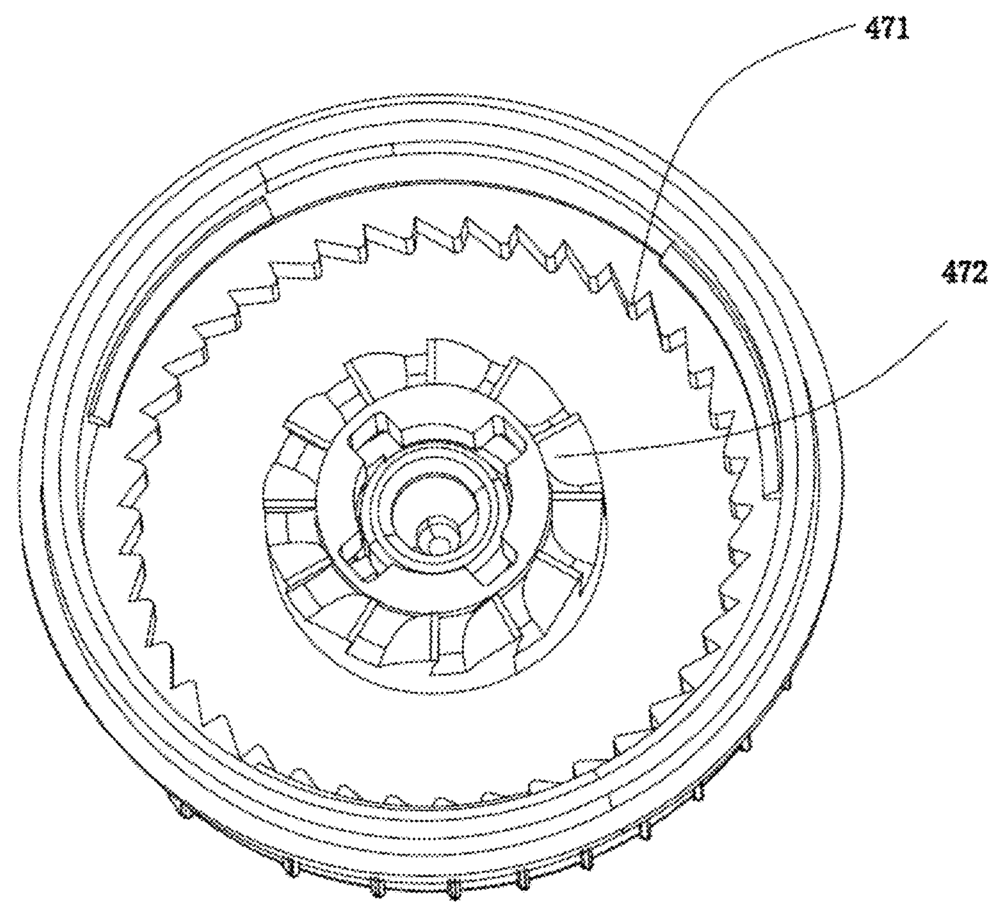
FIG. 13 is a three-dimensional view of a screw cap of a knob assembly in the present disclosure.
Figure 14:
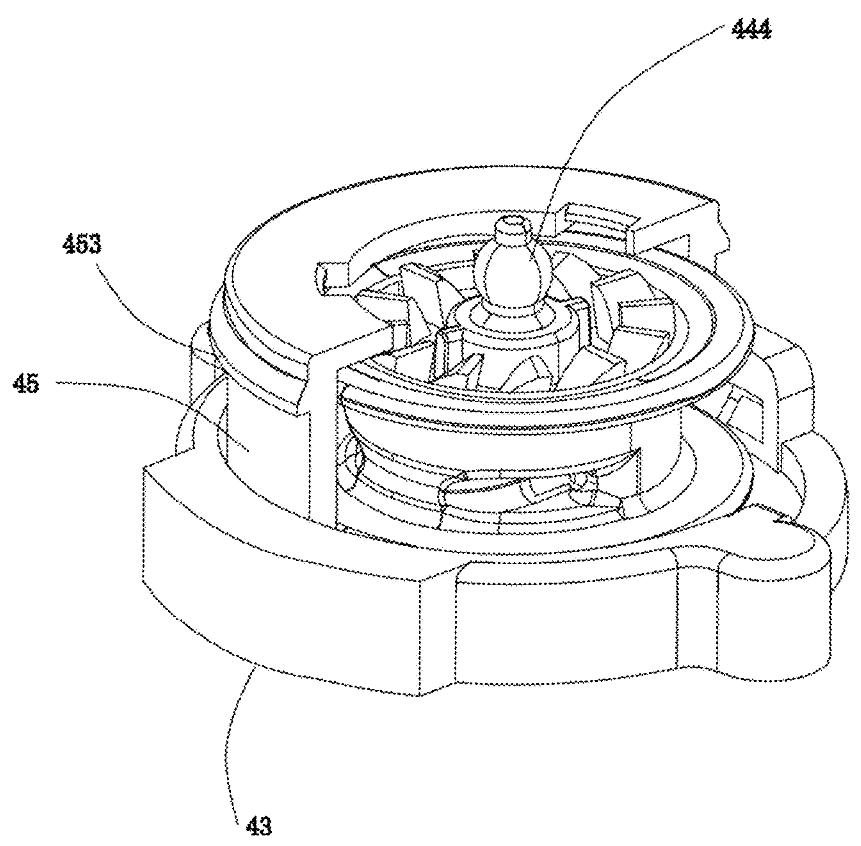
FIG. 14 is an assembly view from the first perspective of a knob assembly in the present disclosure.
Figure 15:
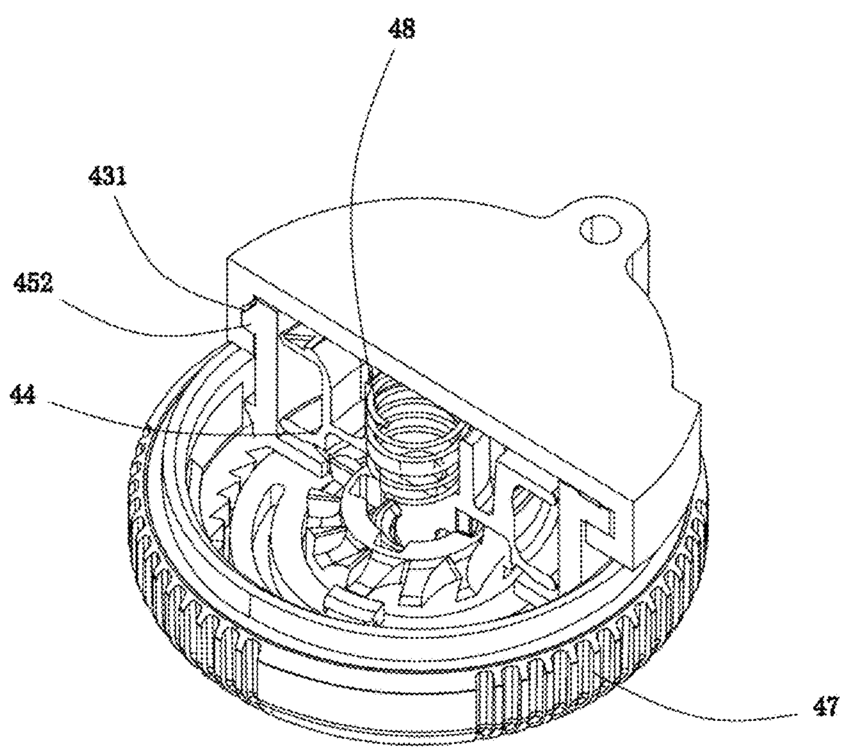
FIG. 15 is an assembly view from the second perspective of a knob assembly in the present disclosure.
Figure 16:
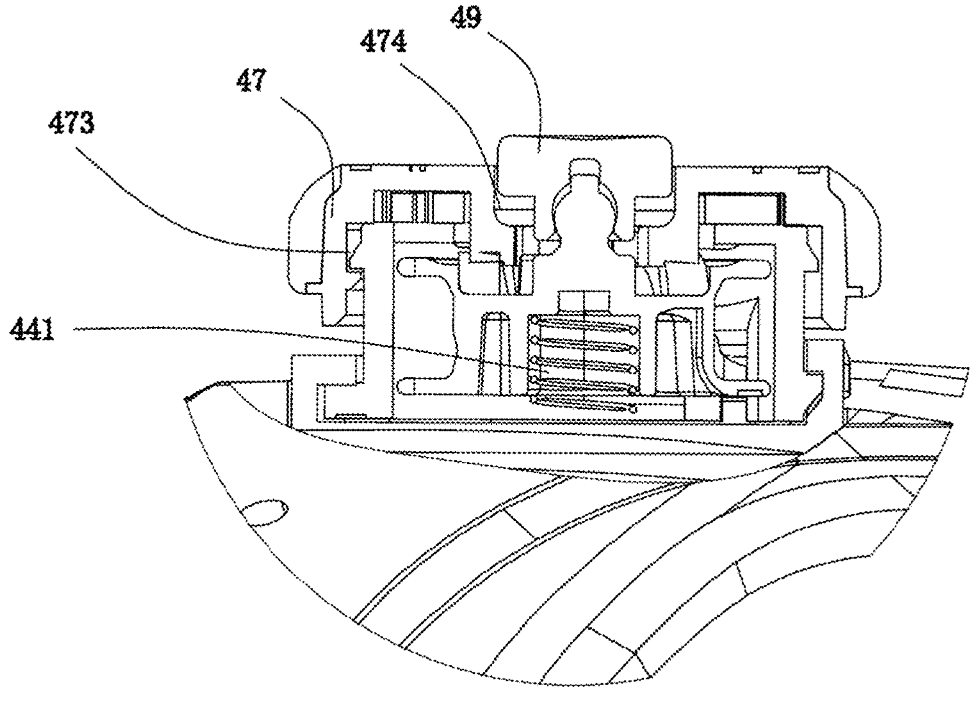
FIG. 16 is a cross-sectional view of a knob assembly in the present disclosure.

Furthermore, the connecting groove 20 may also enable an arched beam integrally formed on the end surface of the second connecting piece 3, and the connecting groove 20 is correspondingly formed on the beam hole of the arched beam. Furthermore, referring to FIG. 7, the arched beam can be configured as disconnected structures.

Figure 5:
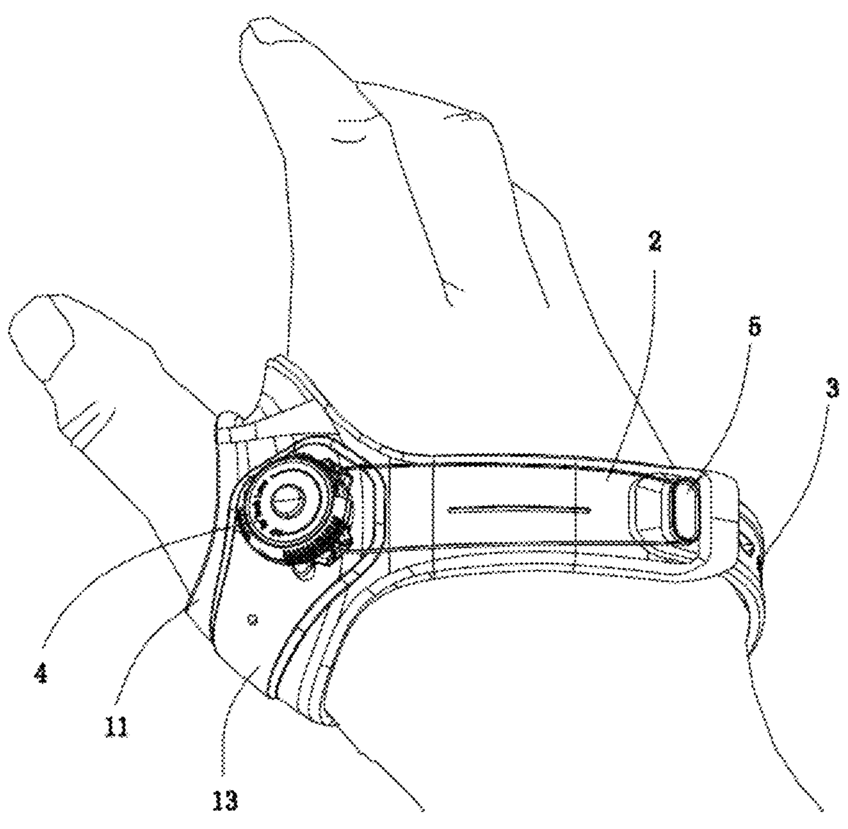
FIG. 5 is a reference diagram showing a state of a back of a hand when using a knob-type thumb protector of the present disclosure.
Figure 6:
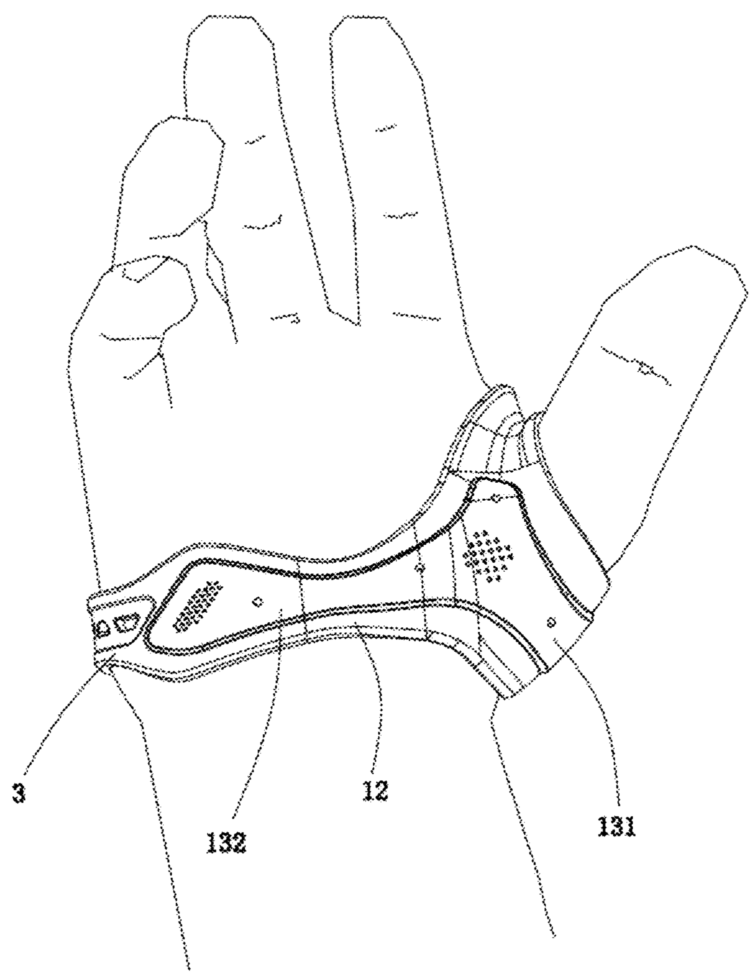
FIG. 6 is a reference diagram showing a state of a palm surface of a hand when using a knob-type thumb protector of the present disclosure.

Please refer to FIG. 5 and FIG. 6. By wearing a knob-type thumb protector, the joint between the thumb and the metacarpal bone is maintained in a fixed shape, which protects the thumb and prevents it from easily deforming due to force, causing muscle or ligament damage. And by means of the knob adjusting piece 4, both ends of the adjusting rope 42, which are sleeved on the hook 5, can pull the hook 5 together simultaneously, allowing for the adjustment of the tightness of the wear. Moreover, the material of the knob-type thumb protector that fits the palm is soft silicone material for comfortable wear. The configuration of the knob-type thumb protector is shaped by the hard supporting piece 13 to maintain its stable shape and improve its strength and durability.

Please refer to FIGS. 8-16. The present disclosure provides a knob adjusting piece 4, which includes a knob assembly 41 and an adjusting rope 42 connected to the knob assembly 41. The knob assembly 41 includes a base 43, a wire reel 44, a sleeve base 45, a ratchet 46, a screw cap 47, a spring 48 and a button 49. The base 43 is fixedly installed on the finger cover portion 11. A holding groove 431 is arranged on the inner side of the peripheral wall of the base 43. The wire reel 44 is rotationally installed on the base 43. Two connected threading holes 441 are arranged on the peripheral wall of the wire reel 44, so that the adjusting rope 42 can enter from one threading hole 441 and then come out from another threading hole 441, and then connect the two ends of the adjusting rope 42 outside the wire reel 44. The adjusting rope 42 forms a closed loop and is connected to the wire reel 44. The two ends of the adjusting rope 42 extending outside the wire reel 44 are driven to rotate together by rotating the wire reel 44, thereby the adjusting rope 42 is winded on the wire reel 44, and the two ends of the line protruding from the wire reel 44 can be retracted and extended in equal lengths at the same time, that is, the two ends of the adjusting rope 42 sleeved on the hook 5 can pull the hook 5 together at the same time. A spring mounting hole 442 with a certain depth is arranged on the center of the bottom surface of the wire reel 44 along the axial direction. A rotating tooth 443 that are annularly distributed around the axis center line and arranged at equal intervals is formed on the top end of the wire reel 44. A sleeve portion 444 is located protruding from the central portion of the top end the wire reel 44. In this embodiment, the sleeve portion 444 adopts a convex ball structure.

The sleeve base 45 is fixedly installed on the base 43, and the sleeve base 45 is provided with a cylindrical portion. An end wall 451 is formed on the upper end of the cylindrical portion, and a through center hole is arranged in the center of the end wall 451. A tenon 452 is formed on the outer peripheral surface of the upper end of the cylindrical portion, and a flange 453 is extended laterally on the outer peripheral surface of the upper end of the cylindrical portion. The sleeve base 45 is sleeved on the outer periphery of the wire reel 44, the tenon 452 extends into the holding groove 431, and the holding groove 431 limits the sleeve base 45 from lifting or rotating relative to the sleeve base 45. Furthermore, two wire passing guide sleeves 454 are arranged on the outer periphery of the sleeve base 45 to match with the two threading holes 441 of the wire reel 44, so that when the adjusting rope 42 is installed, the adjusting rope 42 enters from one wire passing guide sleeve 454 of the sleeve base 45, then passes through the two threading holes 441 on the wire reel 44, and finally passes out from another wire passing guide sleeve 454 of the sleeve base 45. It can be understood that a notch 432 for passing through the corresponding wire passing guide sleeves 454 is arranged on the peripheral wall of the base 43.

The ratchet 46 is fixedly buckled on a top of the sleeve base 45, and a plurality of ratchet teeth 461 are formed on an outer periphery of the ratchet 46, allowing the gear sleeved on the outer periphery of the ratchet teeth 461 to rotate in one direction and preventing the gear from rotating in the opposite direction.

The inner ring surface of the screw cap 47 is provided with a toothed ring 471, which is used to be sleeved on the outer periphery of the ratchet 46 and cooperate with the ratchet teeth 461. The matching teeth 472 that are annularly distributed around the axis center line and arranged at equal intervals is formed on the inner surface of the screw cap 47, to cooperate with the rotating tooth 443 of the wire reel 44. When the matching teeth 472 are inserted into the gap between the rotating teeth 443, the wire reel 44 can be driven to rotate together by rotating the screw cap 47. When the matching teeth 472 are removed from the gap between the rotating teeth 443, the screw cap 47 and the wire reel 44 will not be linked. A clamping groove 473 is formed on the inner ring surface of the screw cap 47, which can be located on the lower side of the toothed ring 471. The clamping groove 473 is clamped between the top surface of the sleeve base 45 and the bottom surface of the flange 453, so that the screw cap 47 can be rotationally installed on the sleeve base 45. A button groove 474 is recessed in the central portion of the top surface of the screw cap 47, and a through hole is formed on the bottom of the button groove 474, allowing the sleeve portion 444 of the wire reel 44 to be extended into the button groove 474.

The spring 48 is installed in the spring mounting hole 442 of the wire reel 44, which provides an elastic force to lift the wire reel 44 upward, so that in a normal state, the top end of the wire reel 44 is abutted against an end wall 451 of the sleeve base 45. The sleeve portion 444 extends into the button groove 474, and at the same time, the matching tooth 472 of the screw cap 47 cooperates with the rotating tooth 443 of the wire reel 44. By rotating the screw cap 47, the wire reel 44 is driven to rotate, thereby realizing pulling and tightening of the adjusting rope 42.

The button 49 is installed in the button groove 474 on the top surface of the screw cap 47 and is fixedly sleeved on the sleeve portion 444. There is a certain movement gap between the bottom surface of the button 49 and the inner portion of the button groove 474. When it is necessary to slacken the adjusting rope 42, by pressing the button 49, the wire reel 44 moves downward, the spring 48 is compressed, and the rotating teeth 443 of the wire reel 44 are disengaged from the matching tooth 472 of the screw cap 47. At this time, the external force acting on the adjusting rope 42 can drive the wire reel 44 to rotate reversely, achieving the slack of the adjusting rope 42. After releasing the button 49, the wire reel 44 will rise under the action of the spring 48, and the rotating teeth 443 of the wire reel 44 will re-cooperate with the matching tooth 472 of the screw cap 47. At this time, the adjusting rope 42 can be tightened by rotating the screw cap 47.

In the preferred embodiment of the present disclosure, the knob adjusting piece 4 adopts the above structure, which is easy to operate; it should be noted that the knob adjusting piece 4 can also have other structures, and can be an existing product directly purchased, as long as the traction adjustment of the adjusting rope 42 can be achieved, that is, as long as the tightening and slacking functions of the rope can be achieved.

As long as it does not violate the idea created by the present disclosure, any combination of various embodiments of the present disclosure shall be regarded as the disclosed content of the present disclosure; within the scope of the technical concept of the present disclosure, any combination of multiple simple variations and different embodiments of the technical solution that do not violate the ideas created in the present disclosure shall be within the scope of protection of the present disclosure.

What is claimed is:

1. A knob-type thumb protector, comprising:

a protector main body, wherein a sleeve hole is formed on the protector main body for a thumb to pass through, so that the protector main body is configured to be sleeved at a base of the thumb to form a structure for supporting the thumb;

a first connecting piece, wherein one end of the first connecting piece is connected to one side of the protector main body, and a connecting groove is arranged on another end of the first connecting piece;

a second connecting piece, wherein one end of the second connecting piece is connected to another side of the protector main body, another end of the second connecting piece for passing through the connecting groove is connected to the first connecting piece, and the second connecting piece cooperates with the first connecting piece to form a ring sleeve that is configured to wrap around a palm; and a knob adjusting piece, wherein the knob adjusting piece includes a knob assembly and an adjusting rope, and the adjusting rope is adjustably connected to the knob assembly; the knob assembly is installed on the protector main body, and one end of the adjusting rope is connected to the end of the second connecting piece that passes through the connecting groove, enabling a tightness of the first connecting piece and a tightness of the second connecting piece to be adjusted by rotating the knob assembly;

wherein the protector main body includes a finger cover portion and a palm supporting portion, the palm supporting portion is connected to the finger cover portion in a belt-like shape, the sleeve hole is formed on the finger cover portion, the knob assembly is installed on the finger cover portion, and the palm supporting portion is used to abut against a palm surface;

a hard supporting piece is arranged on outer surfaces of the finger cover portion and outer surfaces of the palm supporting portion;

the hard supporting piece includes a supporting shell configured to be wrapped around a back side of the thumb and a supporting strip connected to the supporting shell, the supporting shell is arranged on an outer peripheral surface of the finger cover portion, and the supporting strip is arranged on the outer surface of the palm supporting portion.

2. The knob-type thumb protector according to claim 1, wherein the end of the second connecting piece passing through the connecting groove is provided with a hook, so that the adjusting rope is hung on the hook.

3. The knob-type thumb protector according to claim 2, wherein a thumb loop is formed on the sleeve hole, an outer periphery of the base of the thumb is configured to be wrapped by the thumb loop, and the thumb loop has elasticity.

4. The knob-type thumb protector according to claim 1, wherein the finger cover portion, the palm supporting portion, the first connecting piece and the second connecting piece are all made of a flexible material and are integrally formed.

5. The knob-type thumb protector according to claim 1, wherein the hard supporting piece is made of a shaped metal material.

6. The knob-type thumb protector according to claim 1, wherein the knob assembly includes a base, a wire reel, a sleeve base, a ratchet, a screw cap and a spring, the wire reel is rotationally installed on the base, a spring mounting hole is arranged on a bottom surface of the wire reel, a rotating tooth is formed on a top end of the wire reel, the sleeve base is sleeved on an outer periphery of the wire reel, and the sleeve base is fixed on the base;

the ratchet is fixedly buckled on a top of the sleeve base, and a plurality of ratchet teeth are formed on an outer periphery of the ratchet;

the screw cap is rotationally installed on an outer periphery of the sleeve base, and a toothed ring is formed on an inner ring surface of the screw cap; when the screw cap is sleeved on the outer periphery of the ratchet, the toothed ring cooperates with the ratchet teeth, and a matching tooth is formed on an inner surface of the screw cap for cooperating with the rotating tooth of the wire reel; and the spring is installed in the spring mounting hole of the wire reel, and the spring provides an elastic force to lift the wire reel upward, so that in a normal state, the top end of the wire reel is abutted against a top end of the sleeve base, and the matching tooth of the screw cap is cooperated with the rotating tooth of the wire reel; when the wire reel is lowered by a certain displacement due to an external force, the matching tooth is disengaged from the rotating tooth.

7. The knob-type thumb protector according to claim 6, wherein the knob assembly includes a button, and a sleeve portion is protruded from a central portion of the top end of the wire reel, an end wall is formed on an upper end of the sleeve base, and a through center hole is arranged on the end wall; and a button groove is recessed on a top surface of the screw cap, a through hole is formed on a bottom of the button groove, the sleeve portion passes through the through center hole and the through hole and enters the button groove, the button is installed in the button groove, and the button is fixedly sleeved on the sleeve portion.

* * * * *